United States Patent
Boettcher et al.

(10) Patent No.: US 6,537,562 B1
(45) Date of Patent: Mar. 25, 2003

(54) COSMETIC PIT EMULSIONS

(75) Inventors: Axel Boettcher, Rommerskirchen (DE); Hermann Hensen, Haan (DE); Werner Seipel, Hilden (DE)

(73) Assignee: Cognis Deutschland GmbH & Co. KG, Duesseldorf (DE)

( * ) Notice: Subject to any disclaimer, the term of this patent is extended or adjusted under 35 U.S.C. 154(b) by 0 days.

(21) Appl. No.: 09/331,647

(22) PCT Filed: Jan. 20, 1998

(86) PCT No.: PCT/EP98/00279

§ 371 (c)(1),
(2), (4) Date: Jun. 23, 1999

(87) PCT Pub. No.: WO98/32413

PCT Pub. Date: Jul. 30, 1998

(30) Foreign Application Priority Data

Jan. 29, 1997 (DE) .......................... 197 03 087

(51) Int. Cl.[7] ................................. A61K 7/00
(52) U.S. Cl. ................... 424/401; 424/70.19; 514/938
(58) Field of Search ................ 424/401, 70.1, 424/70.19; 514/938

(56) References Cited

U.S. PATENT DOCUMENTS

| | | | |
|---|---|---|---|
| 3,547,828 A | 12/1970 | Mansfield et al. | 252/351 |
| 3,707,535 A | 12/1972 | Baak | 260/210 |
| 3,772,269 A | 11/1973 | Baak | 260/210 |
| 3,839,318 A | 10/1974 | Mansfield | 260/210 |
| 4,172,887 A | 10/1979 | Vanlerberghe et al. | 424/70 |
| 4,349,669 A | 9/1982 | Klahr et al. | 536/127 |
| 5,723,137 A | 3/1998 | Wahle et al. | 424/401 |

FOREIGN PATENT DOCUMENTS

| | | |
|---|---|---|
| CA | 1 334 458 | 2/1995 |
| DE | 11 65 574 | 3/1964 |
| DE | 19 43 689 | 3/1970 |
| DE | 20 36 472 | 2/1971 |
| DE | 20 24 051 | 12/1971 |
| DE | 30 01 064 | 7/1981 |
| DE | 40 23 600 | 1/1992 |
| DE | 43 37 030 | 5/1995 |
| DE | 43 37 041 | 5/1995 |
| DE | 44 21 208 | 12/1995 |
| EP | 0 077 167 | 4/1983 |
| EP | 0 345 586 | 12/1989 |
| FR | 22 52 840 | 6/1975 |
| GB | 962 919 | 7/1964 |
| GB | 1 333 475 | 10/1973 |
| WO | 91/16879 | 11/1991 |
| WO | 93/11865 | 6/1993 |

OTHER PUBLICATIONS

Kosmetische Farbemittel, 1991, pp. 81–106.

*Primary Examiner*—Russell Travers
*Assistant Examiner*—Alyisa Berman
(74) *Attorney, Agent, or Firm*—John E. Drach; Steven J. Trzaska

(57) ABSTRACT

An aqueous cosmetic phase-inversion temperature emulsion containing: (a) a wax ester; (b) a triglyceride; (c) a partial glyceride; and (d) a fatty alcohol polyglycol ether.

13 Claims, No Drawings

COSMETIC PIT EMULSIONS

BACKGROUND OF THE INVENTION

This invention relates to cosmetic PIT emulsions produced by the phase-inversion temperature (PIT) method containing wax esters, triglycerides, glycerides and nonionic surfactants and to their use for the production of refatting systems.

Personal cleansing processes always result in the partial removal of skin and hair lipids. Accordingly, intensive washing of the skin can produce signs of drying out while frequent shampooing of the hair can result in a loss of flexibility. Accordingly, modern cosmetic formulations frequently contain refatting agents to counteract these effects. For example, $C_{12/18}$ fatty acid monoesters and diesters of ethylene oxide/glycerol adducts are known as refatting agents from DE-PS 2024051. German patent application DE-A1 4337041 (Henkel) relates to a process for the production of o/w emulsions by the PIT method in which (a) oils, (b) 0.5 to 30% by weight of nonionic emulsifiers with an HLB value of 12 to 18 and (c) 0.1 to 30% by weight of esters of polyols containing 3 to 6 carbon atoms and fatty acids are used. However, the use of active deodorizing agents, perfume oils or light filters is essential in that case. Unfortunately, known refatting emulsions are attended by the disadvantage that they are unstable and undergo an extreme increase in viscosity, particularly at relatively high storage temperatures. In addition, their refatting effect is often found to have disappeared after prolonged storage. Another problem is that the surfactant content of many cosmetic formulations leads to unwanted solubilization of the refatting emulsions which cannot be counteracted, even by the use of waxes.

Accordingly, the complex problem addressed by the present invention was to provide new refatting systems which would combine excellent performance, i.e. sensorial, properties with high stability in storage. In particular, the refatting systems according to the invention would have a constant viscosity and would remain stable, i.e. would not separate, even when stored at relatively high temperatures. In addition, neither solubilization nor agglomeration would occur in the presence of surfactants.

DESCRIPTION OF THE INVENTION

The present invention relates to cosmetic PIT emulsions containing (a) wax esters,
(b) triglycerides,
(c) partial glycerides and
(d) fatty alcohol polyglycol ethers.

It has surprisingly been found that mixtures of components (a) to (d) almost ideally satisfy the complex requirement profile. The mixtures have excellent refatting and conditioning properties which they retain even in the event of prolonged storage. The emulsions have a constant viscosity and remain stable to separation, even after storage for 4 weeks at 45° C. In the presence of surfactants, no solubilization is observed. The invention includes the observation that the production of the emulsions by the PIT method is a critical parameter so far as their effectiveness is concerned.

Wax Esters

The wax esters which form component (a) are esters of long-chain carboxylic acids with long-chain alcohols which preferably correspond to formula (I):

$$R^1CO\text{—}OR^2 \qquad (I)$$

in which $R^1CO$ is a saturated and/or unsaturated acyl group containing 6 to 22 and preferably 12 to 18 carbon atoms and $R^2$ is an alkyl and/or alkenyl group containing 6 to 22 and preferably 12 to 18 carbon atoms. Typical examples are esters of caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselic acid, linoleic acid, linolenic acid, elaeostearic acid, arachic acid, gadoleic acid, behenic acid and erucic acid and technical mixtures thereof with caproic alcohol, caprylic alcohol, 2-ethylhexyl alcohol, capric alcohol, lauryl alcohol, isotridecyl alcohol, myristyl alcohol, cetyl alcohol, palmitoleyl alcohol, stearyl alcohol, isostearyl alcohol, oleyl alcohol, elaidyl alcohol, petroselinyl alcohol, linolyl alcohol, linolenyl alcohol, elaeostearyl alcohol, arachyl alcohol, gadoleyl alcohol, behenyl alcohol, erucyl alcohol and brassidyl alcohol and technical mixtures thereof. Preferred esters are cetyl palmitate, cetyl stearate, cetyl isostearate, cetyl oleate, cetyl behenate, cetyl erucate, stearyl palmitate, stearyl stearate, stearyl isostearate, stearyl oleate, stearyl behenate, stearyl erucate, isostearyl palmitate, isostearyl stearate, isostearyl isostearate, isostearyl oleate, isostearyl behenate, isostearyl erucate, oleyl palmitate, oleyl stearate, oleyl isostearate, oleyl oleate, oleyl behenate, oleyl erucate, behenyl palmitate, behenyl stearate, behenyl isostearate, behenyl oleate, behenyl behenate, behenyl oleate and mixtures thereof. Esters of the alcohols mentioned with fruit acids, for example malic acid, tartaric acid or citric acid, fruit waxes and silicone waxes may also be used as the wax esters.

Triglycerides

The triglycerides which form component (b) according to the invention are compounds corresponding to formula (II):

$$\begin{array}{l} CH_2O(CH_2CH_2O)_mCOR^3 \\ | \\ CHO(CH_2CH_2O)_nCOR^4 \\ | \\ CH_2O(CH_2CH_2O)_pCOR^5 \end{array} \qquad (II)$$

in which $R^3CO$, $R^4CO$ and $R^5CO$ independently of one another represent linear or branched, saturated and/or unsaturated, optionally hydroxy- and/or epoxy-substituted acyl groups containing 6 to 22 and preferably 12 to 18 carbon atoms and the sum (m+n+p) is 0 or a number of 1 to 100 and preferably 20 to 80. The triglycerides may be of natural origin or may be synthetically produced. They are preferably hydroxyfunctionalized and/or epoxyfunctionalized substances such as, for example, castor oil or hydrogenated castor oil, epoxidized castor oil, ring opening products of epoxidized castor oils having various epoxide numbers with water and addition products of, on average, 1 to 100, preferably 20 to 80 and more preferably 40 to 60 moles with the triglycerides mentioned.

Partial Glycerides

Component (c) may be selected from partial glycerides, i.e. monoglycerides, diglycerides and technical mixtures thereof which may still contain small quantities of triglycerides from their production. The partial glycerides preferably correspond to formula (III):

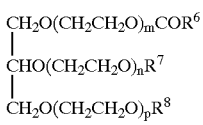

in which R⁶CO is a linear or branched, saturated and/or unsaturated acyl group containing 6 to 22 and preferably 12 to 18 carbon atoms, $R^7$ and $R^8$ independently of one another have the same meaning as $R^6CO$ or represent OH and the sum (m+n+p) is 0 or a number of 1 to 100 and preferably 5 to 25, with the proviso that at least one of the two substituents $R^7$ and $R^8$ represents OH. Typical examples are mono- and/or diglycerides based on caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselic acid, linoleic acid, linolenic acid, elaeostearic acid, arachic acid, gadoleic acid, behenic acid and erucic acid and technical mixtures thereof. Technical lauric acid glycerides, palmitic acid glycerides, stearic acid glycerides, isostearic acid glycerides, oleic acid glycerides, behenic acid glycerides and/or erucic acid glycerides which have a monoglyceride content of 50 to 95% by weight and preferably 60 to 90% by weight are preferably used.

Fatty Alcohol Polyglycol Ethers

Finally, component (d) is selected from fatty alcohol polyglycol ethers corresponding to formula (IV):

$$R^9O(CH_2CH_2O)_qH \quad (IV)$$

in which $R^9$ is a linear or branched alkyl and/or alkenyl group containing 6 to 22 carbon atoms and q is a number of 1 to 50. Typical examples are addition products of, on average, 1 to 50 and preferably 5 to 25 moles of ethylene oxide with caproic alcohol, caprylic alcohol, 2-ethylhexyl alcohol, capric alcohol, lauryl alcohol, isotridecyl alcohol, myristyl alcohol, cetyl alcohol, palmitoleyl alcohol, stearyl alcohol, isostearyl alcohol, oleyl alcohol, elaidyl alcohol, petroselinyl alcohol, linolyl alcohol, linolenyl alcohol, elaeostearyl alcohol, arachyl alcohol, gadoleyl alcohol, behenyl alcohol, erucyl alcohol and brassidyl alcohol and technical mixtures thereof. The surfactants may have both a conventional homolog distribution and a narrow homolog distribution. Addition products of, on average, 10 or 20 moles of ethylene oxide with cetearyl alcohol, stearyl alcohol and/or behenyl alcohol are particularly preferred.

Commercial Applications

In one preferred embodiment, the invention relates to cosmetic PIT emulsions which contain components (a) to (d) in the following quantities:

(a) 25 to 50, preferably 30 to 40% by weight of wax esters,
(b) 1 to 10, preferably 2 to 8% by weight of triglycerides,
(c) 1 to 10, preferably 2 to 8% by weight of partial glycerides and
(d) 1 to 20, preferably 10 to 15% by weight of fatty alcohol polygycol ethers, with the proviso that the quantities shown add up to 100% by weight with water and optionally other typical auxiliaries and additives. The present invention also relates to the use of these PIT emulsions for the production of refatting systems.

The formulations according to the invention, for example hair shampoos, hair lotions, foam baths, cremes, lotions or emollients, may additionally contain mild surfactants, oils, co-emulsifiers, superfatting agents, stabilizers, waxes, consistency regulators, thickeners, cationic polymers, silicone compounds, biogenic agents, antidandruff agents, film formers, preservatives, hydrotropes, solubilizers, UV filters, insect repellents, self-tanning agents, dyes and fragrances as further auxiliaries and additives.

Typical examples of suitable mild surfactants, i.e. surfactants with particular dermatological compatibility, are fatty alcohol polyglycol ether sulfates, monoglyceride sulfates, mono- and/or dialkyl sulfosuccinates, fatty acid isethionates, fatty acid sarcosinates, fatty acid taurides, fatty acid glutamates, ether carboxylic acids, alkyl oligoglucosides, fatty acid glucamides, alkylamidobetaines and/or protein fatty acid condensates, preferably based on wheat proteins.

Suitable oils are, for example, Guerbet alcohols based on fatty alcohols containing 6 to 18 and preferably 8 to 10 carbon atoms, esters of linear $C_{6-22}$ fatty acids with linear $C_{6-22}$ fatty alcohols, esters of branched $C_{6-13}$ carboxylic acids with linear $C_{6-22}$ fatty alcohols, esters of linear $C_{6-22}$ fatty acids with branched alcohols, more particularly 2-ethyl hexanol, esters of linear and/or branched fatty acids with polyhydric alcohols (for example propylene glycol, dimer diol or trimer triol) and/or Guerbet alcohols, triglycerides based on $C_{6-10}$ fatty acids, liquid mono-/di-/triglyceride mixtures based on $C_{6-18}$ fatty acids, esters of $C_{6-22}$ fatty alcohols and/or Guerbet alcohols with aromatic carboxylic acids, more particularly benzoic acid, vegetable oils, branched primary alcohols, substituted cyclohexanes, linear $C_{6-22}$ fatty alcohol carbonates, Guerbet carbonates, esters of benzoic acid with linear and/or branched $C_{6-22}$ alcohols (for example Finsolv® TN), dialkyl ethers, silicone oils and/or aliphatic or naphthenic hydrocarbons.

Suitable co-emulsifiers are, for example, nonionic surfactants from at least one of the following groups:

(1) products of the addition of 2 to 30 moles of ethylene oxide and/or 0 to 5 moles of propylene oxide to linear fatty alcohols containing 8 to 22 carbon atoms, to fatty acids containing 12 to 22 carbon atoms and to alkylphenols containing 8 to 15 carbon atoms in the alkyl group;
(2) glycerol monoesters and diesters and sorbitan monoesters and diesters of saturated and unsaturated fatty acids containing 6 to 22 carbon atoms and ethylene oxide adducts thereof;
(3) alkyl mono- and oligoglycosides containing 8 to 22 carbon atoms in the alkyl group and ethoxylated analogs thereof;
(4) polyol esters and, in particular, polyglycerol esters such as, for example, polyglycerol polyricinoleate or polyglycerol poly-12-hydroxystearate.

Mixtures of compounds from several of these classes are also suitable;

(5) partial esters based on linear, branched, unsaturated or saturated $C_{6/22}$ fatty acids, ricinoleic acid and 12-hydroxystearic acid and glycerol, polyglycerol, pentaerythritol, dipentaerythritol, sugar alcohols (for example sorbitol), alkyl glucosides (for example methyl glucoside, butyl glucoside, lauryl glucoside) and polyglucosides (for example cellulose);
(6) trialkyl phosphates and mono-, di- and/or tri-PEG-alkyl phosphates;
(7) wool wax alcohols;
(8) polysiloxane/polyalkyl polyether copolymers and corresponding derivatives;
(9) mixed esters of pentaerythritol, fatty acids, citric acid and fatty alcohol according to DE-PS 11 65 574 and/or mixed esters of fatty acids containing 6 to 22 carbon atoms, methyl glucose and polyols, preferably glycerol, and
(10) polyalkylene glycols.

The addition products of ethylene oxide and/or propylene oxide with fatty alcohols, fatty acids, alkylphenols, glycerol monoesters and diesters and sorbitan monoesters and diesters of fatty acids or with castor oil are known, commercially available products. They are homolog mixtures of which the average degree of alkoxylation corresponds to the ratio between the quantities of ethylene oxide and/or propylene oxide and substrate with which the addition reaction is carried out.

$C_{8/18}$ alkyl mono- and -oligoglycosides, their production and their use as surfactants are known, for example, from U.S. Pat. Nos. 3,839,318, 3,707,535, 3,547,828, DE-OS 19 43 689, DE-OS 20 36 472 and DE-A1 30 01 064 and EP-A 0 077 167. They are produced in particular by reaction of glucose or oligosaccharides with primary alcohols containing 8 to 18 carbon atoms. So far as the glycoside element is concerned, both monoglycosides where a cyclic sugar unit is attached to the fatty alcohol by a glycoside bond and oligomeric glycosides with a degree of oligomerization of up to preferably about 8 are suitable. The degree of oligomerization is a statistical mean value on which the homolog distribution typical of such technical products is based.

Other suitable co-emulsifiers are zwitterionic surfactants. Zwitterionic surfactants are surface-active compounds which contain at least one quaternary ammonium group and at least one carboxylate and one sulfonate group in the molecule. Particularly suitable zwitterionic surfactants are the so-called betaines, such as the N-alkyl-N,N-dimethyl ammonium glycinates, for example cocoalkyl dimethyl ammonium glycinate, N-acylaminopropyl-N,N-dimethyl ammonium glycinates, for example cocoacylaminopropyl dimethyl ammonium glycinate, and 2-alkyl-3-carboxymethyl-3-hydroxyethyl imidazolines containing 8 to 18 carbon atoms in the alkyl or acyl group and cocoacylaminoethyl hydroxyethyl carboxymethyl glycinate. The fatty acid amide derivative known by the CTFA name of Cocamidopropyl Betaine is particularly preferred. Other suitable emulsifiers are ampholytic surfactants. Ampholytic surfactants are surface-active compounds which, in addition to a $C_{8/18}$ alkyl or acyl group, contain at least one free amino group and at least one —COOH or —SO$_3$H group in the molecule and which are capable of forming inner salts. Examples of suitable ampholytic surfactants are N-alkyl glycines, N-alkyl propionic acids, N-alkylaminobutyric acids, N-alkyliminodipropionic acids, N-hydroxyethyl-N-alkylamidopropyl glycines, N-alkyl taurines, N-alkyl sarcosines, 2-alkylaminopropionic acids and alkylaminoacetic acids containing around 8 to 18 carbon atoms in the alkyl group. Particularly preferred ampholytic surfactants are N-cocoalkylaminopropionate, cocoacylaminoethyl aminopropionate and $C_{12/18}$ acyl sarcosine. Besides the ampholytic emulsifiers, quaternary emulsifiers may also be used, those of the esterquat type, preferably methyl-quaternized difatty acid triethanolamine ester salts, being particularly preferred.

The superfatting agents used may be such substances as, for example, lanolin and lecithin and polyethoxylated or acylated lanolin and lecithin derivatives, polyol fatty acid esters, monoglycerides and fatty acid alkanolamides, the latter also serving as foam stabilizers. Suitable consistency regulators are, above all, fatty alcohols containing 12 to 22 and preferably 16 to 18 carbon atoms and, in addition, partial glycerides. These substances are preferably used in combination with alkyl oligoglucosides and/or fatty acid-N-methyl glucamides of the same chain length and/or polyglycerol poly-12-hydroxystearates. Suitable thickeners are, for example, polysaccharides, more particularly xanthan gum, guar guar, agar agar, alginates and tyloses, carboxymethyl cellulose and hydroxyethyl cellulose, relatively high molecular weight polyethylene glycol monoesters and diesters of fatty acids, polyacrylates (for example Carbopols® [Goodrich] or Syntha-lens® [Sigma]), polyacrylamides, polyvinyl alcohol and polyvinyl pyrrolidone, surfactants such as, for example, ethoxylated fatty acid glycerides, esters of fatty acids with polyols such as, for example, pentaerythritol or trimethylol propane, narrow-range fatty alcohol ethoxylates or alkyl oligoglucosides and electrolytes such as sodium chloride and ammonium chloride.

Suitable cationic polymers are, for example, cationic cellulose derivatives such as, for example, the quaternized hydroxyethyl cellulose available under the name of Polymer JR 400® from Amerchol, cationic starch, copolymers of diallyl ammonium salts and acrylamides, quaternized vinyl pyrrolidone/vinyl imidazole polymers such as, for example, Luviquat® (BASF), condensation products of polyglycols and amines, quaternized collagen polypeptides such as, for example, Lauryldimonium Hydroxypropyl Hydrolyzed Collagen (Lamequat®L Grünau), quaternized wheat polypeptides, polyethyleneimine, cationic silicone polymers such as, for example, Amidomethicone, copolymers of adipic acid and dimethyl aminohydroxypropyl diethylenetriamine (Cartaretine®, Sandoz), copolymers of acrylic acid with dimethyl diallyl ammonium chloride (Merquat® 550, Chemviron), polyamino-polyamides as described, for example, in FR-A 225840 and crosslinked water-soluble polymers thereof, cationic chitin derivatives such as, for example, quaternized chitosan, optionally in microcrystalline distribution, condensation products of dihaloalkyls such as, for example, dibromobutane with bis-dialkylamines such as, for example, bis-dimethylamino-1,3-propane, cationic guar gum such as, for example, Jaguar® CBS, Jaguar® C-17, Jaguar® C-16 of Celanese, quaternized ammonium salt polymers such as, for example, Mirapol® A-15, Mirapol® AD-1, Mirapol® AZ-1 of Miranol.

Suitable silicone compounds are, for example, dimethyl polysiloxanes, methyl phenyl polysiloxanes, cyclic silicones and amino-, fatty acid-, alcohol-, polyether-, epoxy-, fluorine- and/or alkyl-modified silicone compounds which may be both liquid and resin-like at room temperature. Typical examples of fats are glycerides while suitable waxes are inter alia beeswax, carnauba wax, candelilla wax, montan wax, paraffin wax or microwaxes, optionally in combination with hydrophilic waxes, for example cetostearyl alcohol, or partial glycerides. The pearlescent waxes used may be, in particular, mono- and difatty acid esters of polyalkylene glycols, partial glycerides or esters of fatty alcohols with polybasic carboxylic acids or hydroxycarboxylic acids. Suitable stabilizers are metal salts of fatty acids such as, for example, magnesium, aluminium and/or zinc stearate. Biogenic agents in the context of the invention are, for example, tocopherol, tocopherol acetate, tocopherol palmitate, ascorbic acid, retinol, bisabolol, allantoin, phytantriol, panthenol, AHA acids, aminoacids, ceramides, pseudoceramides, essential oils, plant extracts and vitamin complexes. Suitable antidandruff agents are climbazol, octopirox and zinc pyrethion. Typical film formers are, for example, chitosan, microcrystalline chitosan, quaternized chitosan, polyvinyl pyrrolidone, vinyl pyrrolidone/vinyl acetate copolymers, polymers of the acrylic acid series, quaternary cellulose derivatives, collagen, hyaluronic acid and salts thereof and similar compounds. Montmorillonites, clay minerals, Pemulen and alkyl-modified Carbopols (Goodrich) may be used as swelling agents for aqueous phases.

In the context of the invention, UV filters are organic compounds which are capable of absorbing ultraviolet rays and of releasing the energy absorbed in the form of longer wave radiation, for example heat. Typical examples are 4-aminobenzoic acid and esters and derivatives thereof (for example 2-ethylhexyl-p-dimethylaminobenzoate or p-dimethylaminobenzoic acid octyl ester), methoxycinnamic acid and derivatives thereof (for example 4-methoxycinnamic acid-2-ethylhexyl ester), benzophenones (for example oxybenzone, 2-hydroxy-4-methoxybenzophenone), dibenzoyl methanes, salicylate esters, 2-phenyl benzimidazole-5-sulfonic acid, 1-(4-tert.butylphenyl)-3-(4'-methoxyphenyl)-propane-1,3-dione, 3-(4'-methyl)-benzylidenebornan-2-one, methylbenzylidene camphor and the like. Other suitable UV filters are finely disperse metal oxides and salts, for example titanium dioxide, zinc oxide, iron oxide, aluminium oxide, cerium oxide, zirconium oxide, silicates (talcum) and barium sulfate. The particles should have an average diameter of less than 100 nm, preferably from 5 to 50 nm and more preferably from 15 to 30 nm. They may be spherical in shape although ellipsoidal particles or other non-spherical particles may also be used. Besides the two above-mentioned groups of primary light filters, secondary light filters of the antioxidant type, which interrupt the photochemical reaction chain initiated when UV radiation penetrates into the skin, may also be used. Typical examples of these secondary light filters are Superoxid-Dismutase, tocopherols (vitamin E) and ascorbic acid (vitamin C).

In addition, hydrotropes such as, for example, ethanol, isopropyl alcohol or polyols may be used to improve flow behavior. Suitable polyols preferably contain 2 to 15 carbon atoms and at least two hydroxyl groups. Typical examples are glycerol;

alkylene glycols such as, for example, ethylene glycol, diethylene glycol, propylene glycol, butylene glycol, hexylene glycol and polyethylene glycols having an average molecular weight of 100 to 1,000 dalton;

technical oligoglycerol mixtures with a degree of self-condensation of 1.5 to 10 such as, for example, technical diglycerol mixtures with a diglycerol content of 40 to 50% by weight;

methylol compounds such as, in particular, trimethylol ethane, trimethylol propane, trimethylol butane, pentaerythritol and dipentaerythritol;

lower alkyl glucosides, particularly those containing 1 to 8 carbon atoms in the alkyl group, for example methyl and butyl glucoside;

sugar alcohols containing 5 to 12 carbon atoms such as, for example, sorbitol or mannitol;

sugars containing 5 to 12 carbon atoms such as, for example, glucose or sucrose and aminosugars such as, for example, glucamine.

Suitable preservatives are, for example, phenoxyethanol, formaldehyde solution, parabens, pentanediol or sorbic acid. Suitable insect repellents are N,N-diethyl-m-toluamide, pentane-1,2-diol or Insect Repellent 3535. A suitable self-tanning agent is dihydroxyacetone. Suitable dyes are any of the substances suitable and licensed for cosmetic purposes as listed, for example, in the publication "Kosmetische F ärbemittel" of the Farbstoff-kommission der Deutschen Forschungsgemeinschaft, Verlag Chemie, Weinheim, 1984, pages 81 to 106, These dyes are normally used in concentrations of 0.001 to 0.1% by weight, based on the mixture as a whole. The total percentage content of auxiliaries and additives may be from 1 to 50% by weight and is preferably from 5 to 40% by weight, based on the particular formulation.

EXAMPLES

Refatting systems varying in their composition were performance-tested. The viscosity of the formulations was measured by the Brookfield method in an RVF viscosimeter (spindle 1, 10 r.p.m.) both immediately after production (20° C.) and after storage for 4 weeks at 45° C. The stability of the formulations was optically determined after storage (4 weeks at 45° C.). In this connection, "+" means stable while "−" means phase separation. The refatting effect was subjectively evaluated by a panel of trained volunteers. 1=very good and 3=average. The result is expressed as the average value of 5 measurements for a given formulation immediately after its production and for the same formulation after storage (for 4 weeks for 45° C.). The results are set out in Table 1. Formulations F1 and F2 correspond to the invention while formulations F3 to F6 are intended for comparison.

TABLE 1

Performance of refatting systems (quantities as % by weight)

| Composition/performance | F1 | F2 | F3 | F4 | F5 | F6 |
|---|---|---|---|---|---|---|
| Cetyl palmitate | 30 | 40 | 30 | 30 | 30 | — |
| Hydrogenated castor oil | 4 | 6 | — | 4 | 4 | 4 |
| Glceryl stearate | 2 | 3 | 6 | — | 10 | 30 |
| Beheneth-10 | 8 | 12 | 8 | 10 | — | 10 |
| Water | | | to 100 | | | |
| Viscosity-immediately [mpas] | 6,000 | 6,400 | 6,000 | 5,800 | 6,200 | 6,000 |
| Viscosity-after storage [mPas] | 6,100 | 6,400 | 12,000 | 17,000 | 15,000 | 12,000 |
| Stability | + | + | — | — | — | — |
| Refatting effect-immediately | 1.0 | 1.5 | 1.5 | 2.0 | 3.0 | 3.0 |
| Refatting effect-after storage | 1.0 | 1.5 | 3.0 | 3.0 | 3.0 | 3.0 |

What is claimed is:

1. An aqueous cosmetic phase-inversion temperature emulsion comprising:
   (a) from 30 to 40% by weight, based on the weight of the emulsion, of a wax ester;
   (b) a triglyceride;
   (c) a partial glyceride; and
   (d) a fatty alcohol polyglycol ether.

2. The emulsion of claim 1 wherein the wax ester corresponds to formula I:

$$R^1CO\text{—}OR^2 \tag{I}$$

wherein $R^1CO$ is a saturated or unsaturated acyl group containing from 6 to 22 carbon atoms and $R^2$ is an alkyl or alkenyl group containing from 6 to 22 carbon atoms.

3. The emulsion of claim 1 wherein the triglyceride corresponds to formula II:

$$\begin{array}{l} CH_2O(CH_2CH_2O)_mCOR^3 \\ | \\ CHO(CH_2CH_2O)_nCOR^4 \\ | \\ CH_2O(CH_2CH_2O)_pCOR^5 \end{array} \tag{II}$$

wherein $R^3CO$, $R^4CO$, and $R^5CO$, independently of one another, represent a linear or branched, saturated or unsaturated, optionally hydroxy- or epoxy-substituted acyl group containing from 6 to 22 carbon atoms, and the sum of (m+n+p) is 0 or a number from 1 to 100.

4. The emulsion of claim 1 wherein the partial glyceride corresponds to formula III:

$$CH_2O(CH_2CH_2O)_mCOR^6 \\ | \\ CHO(CH_2CH_2O)_nR^7 \\ | \\ CH_2O(CH_2CH_2O)_pR^8 \qquad \text{(III)}$$

wherein $R^6CO$ is a linear or branched, saturated or unsaturated, optionally hydroxy- or epoxy-substituted acyl group containing from 6 to 22 carbon atoms, $R^7$ and $R^8$, independently of one another has the same meaning as $R^8CO$ or represent OH, and the sum of (m+n+p) is 0 or a number from 1 to 100, with the proviso that at least one of $R^7$ and $R^8$ represents OH.

5. The emulsion of claim 1 wherein the fatty alcohol polyglycol ether corresponds to formula IV:

$$R^8O(CH_2CH_2O)_qH \qquad \text{(IV)}$$

wherein $R^8$ is a linear or branched alkyl or alkenyl group containing from 6 to 22 carbon atoms and q is a number from 1 to 50.

6. The emulsion of claim 1 comprising:
   (a) from 30 to 40% by weight of the wax ester;
   (b) from 1 to 10% by weight of the triglyceride;
   (c) from 1 to 10 by weight of the partial glyceride; and
   (d) from 1 to 10 by weight of the fatty alcohol polyglycol ether, all weights being based on the total weight of the aqueous emulsion.

7. A personal cleansing composition comprising the aqueous cosmetic phase-inversion temperature emulsion of claim 1.

8. A process for enhancing refatting properties of a personal cleansing composition comprising adding an effective amount of an aqueous phase-inversion temperature emulsion to the personal cleansing composition, the emulsion containing:
   (a) from 30 to 40% by weight, based on the weight of the emulsion, of a wax ester;
   (b) a triglyceride;
   (c) a partial glyceride: and
   (d) a fatty alcohol polyglycol ether.

9. The process of claim 8 wherein the wax ester corresponds to formula I:

$$R^1CO-OR^2 \qquad \text{(I)}$$

wherein $R^1CO$ is a saturated or unsaturated acyl group containing from 6 to 22 carbon atoms and $R^2$ is an alkyl or alkenyl group containing from 6 to 22 carbon atoms.

10. The process of claim 8 wherein the triglyceride corresponds to formula II:

$$CH_2O(CH_2CH_2O)_mCOR^3 \\ | \\ CHO(CH_2CH_2O)_nCOR^4 \\ | \\ CH_2O(CH_2CH_2O)_pCOR^5 \qquad \text{(II)}$$

wherein $R^3CO$, $R^4CO$, and $R^6CO$, independently of one another, represent a linear or branched, saturated or unsaturated, optionally hydroxy- or epoxy-substituted acyl group containing from 6 to 22 carbon atoms, and the sum of (m+n+p) is 0 or a number from 1 to 100.

11. The process of claim 8 wherein the partial glyceride corresponds to formula III:

$$CH_2O(CH_2CH_2O)_mCOR^6 \\ | \\ CHO(CH_2CH_2O)_nR^7 \\ | \\ CH_2O(CH_2CH_2O)_pR^8 \qquad \text{(III)}$$

wherein $R^6CO$ is a linear or branched, saturated or unsaturated, optionally hydroxy- and/or epoxy-substituted acyl group containing from 6 to 22 carbon atoms, $R^7$ and $R^8$ independently of one another has the same meaning as $R^6CO$ or represent OH, and the sum of (m+n+p) is 0 or a number from 1 to 100, with the proviso that at least one of $R^7$ and $R^8$ represents OH.

12. The process of claim 8 wherein the fatty alcohol polyglycol ether corresponds to formula IV:

$$R^8O(CH_2CH_2O)_qH \qquad \text{(IV)}$$

wherein $R^9$ is a linear or branched alkyl or alkenyl group containing from 6 to 22 carbon atoms and q is a number from 1 to 50.

13. The process of claim 8 wherein the emulsion comprises:
   (a) from 30 to 40% by weight of the wax ester;
   (b) from 1 to 10% by weight of the triglyceride;
   (c) from 1 to 10% by weight of the partial glyceride; and
   (d) from 1 to 10% by weight of the fatty alcohol polyglycol ether, all weights being based on the total weight of the aqueous emulsion.

* * * * *